United States Patent
Matsusue

(10) Patent No.: US 11,220,787 B2
(45) Date of Patent: Jan. 11, 2022

(54) FINE CELLULOSE FIBER-CONTAINING SUBSTANCE, METHOD FOR MANUFACTURING THE SAME, AND FINE CELLULOSE FIBER DISPERSION

(71) Applicant: Daio Paper Corporation, Ehime (JP)

(72) Inventor: Ikko Matsusue, Ehime (JP)

(73) Assignee: Daio Paper Corporation, Ehime (JP)

( * ) Notice: Subject to any disclaimer, the term of this patent is extended or adjusted under 35 U.S.C. 154(b) by 72 days.

(21) Appl. No.: 16/632,799

(22) PCT Filed: May 30, 2018

(86) PCT No.: PCT/JP2018/020737
§ 371 (c)(1),
(2) Date: Jan. 21, 2020

(87) PCT Pub. No.: WO2019/021619
PCT Pub. Date: Jan. 31, 2019

(65) Prior Publication Data
US 2021/0156090 A1    May 27, 2021

(30) Foreign Application Priority Data
Jul. 24, 2017   (JP) .............................. JP2017-142795

(51) Int. Cl.
*D21H 11/20* (2006.01)
*D21C 9/00* (2006.01)

(52) U.S. Cl.
CPC ............ *D21H 11/20* (2013.01); *D21C 9/004* (2013.01)

(58) Field of Classification Search
USPC ..................................................... 162/157.6
See application file for complete search history.

(56) References Cited

U.S. PATENT DOCUMENTS

| | | |
|---|---|---|
| 5,698,265 A | 12/1997 | Mucalo et al. |
| 2011/0196139 A1 | 8/2011 | Lee et al. |
| 2019/0177916 A1* | 6/2019 | Mizukami ................ C08K 3/10 |

FOREIGN PATENT DOCUMENTS

| | | |
|---|---|---|
| CA | 2976452 | 8/2016 |
| JP | 46-10551 | 3/1971 |
| JP | H09-165402 | 3/1999 |
| JP | 2013-127141 | 6/2013 |
| JP | 2014-118521 | 6/2014 |
| JP | 2015-189698 | 11/2015 |
| JP | 2016-527330 | 9/2016 |
| JP | 2017-2231 | 1/2017 |
| JP | 2017-052943 | 3/2017 |
| WO | 2016/133076 | 8/2016 |
| WO | 2017/170908 | 10/2017 |
| WO | 2018/038194 | 3/2018 |

OTHER PUBLICATIONS

International Search Report for PCT/JP2018/020737, dated Aug. 14, 2018.
PCT Third Party Observation for PCT/JP2018/020737, dated Sep. 2, 2019.
"Modification of Cellulose Phosphonatewith N, N-Dimethylacrylamide and4-Vinylpyridine, and Flame-RetardantProperties of the Products", NorihiroInagaki et al, Journal of PolymerScience:Polymer Chemistry Edition, vol. 16p. 2771-p. 2779.
Office Action issued in Corresponding Chinese Patent Application No. 201880048437, dated Aug. 12, 2021.

* cited by examiner

*Primary Examiner* — Mark Halpern
(74) *Attorney, Agent, or Firm* — Andrus Intellectual Property Law, LLP

(57) ABSTRACT

A fine cellulose fiber-containing substance that has excellent dispersibility in water and can be manufactured easily. A method is for manufacturing the fine cellulose fiber-containing substance, and a method is for manufacturing a fine cellulose fiber dispersion. A fine cellulose fiber-containing substance contains fine cellulose fibers into which a phosphite containing a cation of an inorganic substance is introduced. The ratio of the cation of the inorganic substance with respect to 1 g of the fine cellulose fibers is 0.14 mmol or more. In manufacturing the fine cellulose fiber-containing substance, a phosphite is introduced into cellulose fibers, and then the cellulose fibers are defibrated to obtain a dispersion containing fine cellulose fibers, during which an alkali metal ion-containing substance is added to the cellulose fibers, and the dispersion is concentrated. In manufacturing a fine cellulose fiber dispersion, the fine cellulose fiber-containing substance is mixed with water.

7 Claims, No Drawings

FINE CELLULOSE FIBER-CONTAINING SUBSTANCE, METHOD FOR MANUFACTURING THE SAME, AND FINE CELLULOSE FIBER DISPERSION

CROSS-REFERENCE TO RELATED APPLICATIONS

This application is the U.S. national stage application of International Application PCT/JP2018/020737, filed May 30, 2018, which international application was published on Jan. 31, 2019, as International Publication WO 2019/021619 in the Japanese language. The International Application claims priority of Japanese Patent Application No. 2017-142795, filed Jul. 24, 2017. The international application and Japanese application are both incorporated herein by reference, in entirety.

TECHNICAL FIELD

The present invention relates to a fine cellulose fiber-containing substance, a method for manufacturing the same, and a method for manufacturing a fine cellulose fiber dispersion.

BACKGROUND ART

In recent years, attention has been paid to nanotechnology aimed at making a substance finer to a nanometer level such that the substance has new physical properties different from conventional properties. Above all, fine cellulose fibers manufactured from pulp are excellent in strength, elasticity, heat stability, and the like, and also contributes to environmental protection. Therefore, expectation for the fine cellulose fibers is large, and an application range thereof is wide. Examples thereof include industrial applications such as a filter material, a filter aid, a base material for an ion exchanger, a filler for a chromatography analyzer, and a filler for blending resins and rubbers, and applications for a blending agent of cosmetics such as a lipstick, powder cosmetics, and emulsified cosmetics. The fine cellulose fibers also have excellent aqueous dispersibility. From this property, for example, use in applications such as food, cosmetics, a viscosity retention agent for a paint or the like, a strengthening agent for a food raw material dough, a moisture retention agent, a food stabilizer, a low-calorie additive, and an emulsion stabilization aid is also expected.

Such fine cellulose fibers expected to be used in various applications are usually obtained by making pulp or the like in a water-dispersed state finer. Therefore, the obtained fine cellulose fibers are in a water-dispersed state (dispersion). However, when the fine cellulose fibers are in a dispersion state, a large amount of transportation energy is required. Therefore, it is necessary to dry the dispersion of the fine cellulose fibers in view of commercialization. However, when the fine cellulose fibers are dried, the fine cellulose fibers are strongly aggregated by hydrogen bonding. For this reason, even when the dried fine cellulose fibers are dispersed again in water, the fine cellulose fibers are not sufficiently dispersed as compared with the state before drying disadvantageously. Therefore, a technique for improving dispersibility (redispersibility) of fine cellulose fibers in a dispersion medium such as water is required.

In this regard, for example, Patent Literature 1 proposes "a method for manufacturing a cellulose nanofiber dispersion, including: a step of mixing cellulose nanofibers with a redispersion accelerator to obtain a gelatinized body; and a step of mixing the gelatinized body, an organic liquid compound, and a dispersing agent to redisperse the cellulose nanofibers". However, this proposal does not dry fine cellulose fibers to a dry state, but merely manufactures a gelatinized body. Moreover, this proposal assumes an organic liquid compound as a dispersion medium.

Patent Literature 2 proposes "a method for drying bacterial cellulose, characterized in that a third component other than bacterial cellulose and water is added to an aqueous suspension containing bacterial cellulose, and then the resulting mixture is dehydrated and dried". However, bacterial cellulose is cellulose produced by microorganisms, and has different physical properties and the like from fine cellulose fibers that can be obtained by defibrating pulp. Therefore, even when this proposal is applied to drying of fine cellulose fibers, a similar effect is not necessarily obtained.

Patent Literature 3 proposes "a method for manufacturing a fine fibrous cellulose redispersion slurry, including: a first step of adding a compound containing at least one kind selected from an alkali soluble metal and a polyvalent metal ion to a fine fibrous cellulose slurry to obtain a fine fibrous cellulose concentrate; and a second step of adding at least one kind selected from tetraalkyl onium hydroxide and alkyl amine to the fine fibrous cellulose concentrate". However, according to this proposal, the step of obtaining a fine cellulose fiber concentrate is complicated. In addition, since an alcohol solution is used for redispersion, a handling property at the time of use of a dispersion after redispersion is poor.

CITATION LIST

Patent Literature

Patent Literature 1: JP 2014-118521 A
Patent Literature 2: JP 9-165402 A
Patent Literature 3: JP 2017-52943 A

SUMMARY OF INVENTION

Technical Problem

A main problem to be solved by the present invention is to provide a fine cellulose fiber-containing substance that has excellent dispersibility in water and can be manufactured easily, a method for manufacturing the fine cellulose fiber-containing substance, and a method for manufacturing a fine cellulose fiber dispersion.

Solution to Problem

A means for solving the above problem includes
a fine cellulose fiber-containing substance containing fine cellulose fibers into which a phosphite containing a cation of an inorganic substance is introduced,
in which the ratio of the cation of the inorganic substance with respect to 1 g of the fine cellulose fibers is 0.14 mmol or more.

In addition, the means for solving the above problem includes
a method for manufacturing a fine cellulose fiber-containing substance, the method including:
introducing a phosphite into cellulose fibers, and then defibrating the cellulose fibers to obtain a dispersion containing fine cellulose fibers, during which an alkali metal ion-containing substance is added to the cellulose fibers; and concentrating the dispersion to obtain a fine cellulose fiber-containing substance.

Furthermore, the means for solving the above problem includes a method for manufacturing a fine cellulose fiber dispersion, the method including mixing the fine cellulose fiber-containing substance with water.

Advantageous Effects of Invention

The present invention provides a fine cellulose fiber-containing substance that has excellent dispersibility in water and can be manufactured easily, a method for manufacturing the fine cellulose fiber-containing substance, and a method for manufacturing a fine cellulose fiber dispersion.

DESCRIPTION OF EMBODIMENTS

Next, an embodiment for carrying out the present invention will be described. Note that the present embodiment is an example of the present invention.

A fine cellulose fiber-containing substance of the present embodiment contains fine cellulose fibers into which a phosphite containing a cation of an inorganic substance is introduced. In manufacturing the fine cellulose fiber-containing substance, a phosphite is introduced into cellulose fibers, and then the cellulose fibers are defibrated to obtain a dispersion containing fine cellulose fibers, during which an alkali metal ion-containing substance is added to the cellulose fibers, and the dispersion is concentrated. Hereinafter, description will be made in order. Note that the addition of the alkali metal ion-containing substance is performed in a step of introducing a phosphite or a step prior to this step. However, the addition of the alkali metal ion-containing substance can also be performed in, for example, a defibration step, a concentration step, or an aggregation step.

(Fine Cellulose Fibers)

The fine cellulose fibers into which a phosphite containing a cation of an inorganic substance is introduced according to the present embodiment (hereinafter, also referred to simply as "fine cellulose fibers") are obtained by substituting functional groups represented by the following structural formula (1) for a part of hydroxy groups (—OH groups) of cellulose fibers to introduce a phosphite containing a cation of an inorganic substance (to perform modification or denaturation) (to perform esterification). The cellulose fibers are preferably obtained by substituting carbamate groups for a part of hydroxy groups of cellulose fibers to introduce also carbamates (esters of carbamic acid).

[Chemical formula 1]

Structural formula (1)

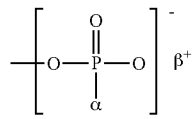

In structural formula (1), a represents any one of nothing, R, and NHR. R represents any one of a hydrogen atom, a saturated-linear hydrocarbon group, a saturated-branched hydrocarbon group, a saturated-cyclic hydrocarbon group, an unsaturated-linear hydrocarbon group, an unsaturated-branched hydrocarbon group, an aromatic group, and a derived group thereof. β represents a cation of an inorganic substance.

The phosphite is a compound in which a hydroxyl group (hydroxy group) (–OH) and an oxo group (=O) are bonded to a phosphorus atom, and the hydroxyl group gives an acidic proton. Therefore, the phosphite is a type of oxo acid of phosphorus. Therefore, the phosphite has a high negative charge similarly to a compound having a phosphate group. Therefore, when the phosphite is introduced, repulsion between cellulose molecules is increased, and defibration of the cellulose fibers is easy. When the phosphite is introduced, transparency and viscosity of the dispersion are improved. In particular, when a carbamate is also introduced together with the phosphite, the transparency and viscosity are further improved. In this regard, the carbamate has an amino group. Therefore, by the introduction of the carbamate, the fine cellulose fibers also have a positive charge. Therefore, it is considered that the introduction of the carbamate increases a charge interaction between the phosphite and the carbamate and increases the viscosity. Note that the carbamate is more easily introduced when the phosphite is introduced than when a compound having a phosphate group is introduced at the same time.

Furthermore, when the phosphite is introduced, yellowing of obtained fine cellulose fibers is prevented unlike a case where a compound having a phosphate group is introduced. In this regard, the effect of preventing yellowing is not obtained by introducing a general oxo acid of phosphorus, but is obtained only by introducing the phosphite. Therefore, the concept of an oxo acid of phosphorus has no meaning from a viewpoint of preventing yellowing. The present inventors have independently found that the phosphite has a yellowing preventing effect.

Note that the present inventors consider that yellowing is likely to occur when a compound having a phosphate group is introduced because a double bond is easily generated in cellulose by a Maillard reaction or a reduction reaction. Since a compound having a phosphate group has a larger number of hydrogen atoms than the phosphite, the pH is lowered. The lower the pH is, the more easily a reaction between an amine and a sugar occurs, or the more easily cellulose is reduced. Therefore, when an attempt is made to introduce a compound having a phosphate group, cellulose is decomposed at the time of heating to easily generate a sugar, or cellulose is easily reduced. As a result, it is considered that yellowing is more likely to occur when a compound having a phosphate group is introduced.

The introduction amount of the phosphite is preferably 0.06 to 3.39 mmol, more preferably 0.61 to 1.75 mmol, and particularly preferably 0.95 to 1.42 mmol with respect to 1 g of fine cellulose fibers. When the introduction amount is less than 0.06 mmol, defibration of the cellulose fibers may be difficult. In addition, the aqueous dispersion of the fine cellulose fibers may be unstable. Meanwhile, when the introduction amount exceeds 3.39 mmol, the cellulose fibers may be dissolved in water.

The introduction amount of the phosphite is a value evaluated on the basis of elemental analysis. For this elemental analysis, X-Max 50 001 manufactured by Horiba, Ltd. is used.

The degree of substitution (DS) of a functional group represented by structural formula (1) is preferably 0.01 to 0.55, more preferably 0.10 to 0.28, and particularly preferably 0.15 to 0.23. When the degree of substitution is less than 0.01, defibration of the cellulose fibers may be difficult. Meanwhile, when the degree of substitution exceeds 0.55, the cellulose fibers may turn yellow.

The degree of substitution of the carbamate group is preferably 0.01 to 0.50, more preferably 0.05 to 0.45, and particularly preferably 0.10 to 0.40. When the degree of substitution is less than 0.01, the transparency and viscosity are not necessarily increased sufficiently. Meanwhile, when the degree of substitution exceeds 0.50, the cellulose fibers may turn yellow.

The degree of substitution refers to the average number of substitutions of functional groups (a functional group represented by structural formula (1) or a carbamate group) with respect to one glucose unit in cellulose. The degree of substitution can be controlled, for example, by reaction temperature or reaction time. Increasing the reaction temperature or increasing the reaction time increases the degree of substitution. However, when the degree of substitution is too high, the degree of polymerization of cellulose is significantly reduced.

The ratio (content) of a cation of an inorganic substance with respect to 1 g of the fine cellulose fibers is preferably 0.14 mmol or more, and more preferably 0.69 mmol or more. When the ratio of a cation of an inorganic substance is less than 0.14 mmol, redispersibility in water is not necessarily increased sufficiently.

The fiber width of each of the fine cellulose fibers (average diameter of a single fiber) is preferably 1 to 1000 nm, more preferably 2 to 400 nm, and particularly preferably 3 to 100 nm. When the fiber width is less than 1 nm, cellulose is dissolved in water, and the fine cellulose fibers do not necessarily have physical properties as fine cellulose fibers, such as strength, rigidity, or dimensional stability. Meanwhile, when the fiber width exceeds 1000 nm, the cellulose fibers cannot be said to be fine cellulose fibers, but become normal cellulose fibers.

The fiber width of each of the fine cellulose fibers is measured using an electron microscope as follows.

First, 100 ml of an aqueous dispersion of fine cellulose fibers having a solid concentration of 0.01 to 0.1% by mass is filtered through a Teflon (registered trademark) membrane filter, and solvent substitution is performed once with 100 ml of ethanol and three times with 20 ml of t-butanol. Next, the resulting product is lyophilized and coated with osmium to obtain a sample. This sample is observed with an electron microscope SEM image at a magnification of 5000, 10000, or 30000 depending on the width of a fiber forming the sample. In this observation, two diagonals are drawn on the observation image, and three arbitrary straight lines passing through an intersection of the diagonals are further drawn. Then, the widths of 100 fibers in total intersecting the three straight lines are visually measured. A median diameter of these measured values is defined as a fiber width.

The axial ratio (fiber length/fiber width) of each of the fine cellulose fibers is preferably 3 to 1,000,000, more preferably 6 to 340,000, and particularly preferably 10 to 340,000. When the axial ratio is less than 3, the fine cellulose fibers cannot be said to be fibrous. Meanwhile, when the axial ratio exceeds 1,000,000, the viscosity of the dispersion (slurry) may be too high.

The degree of crystallinity of the fine cellulose fibers is preferably 50 to 100%, more preferably 60 to 90%, and particularly preferably 65 to 85%. When the degree of crystallinity is less than 50%, strength and heat resistance may be insufficient. The degree of crystallinity can be adjusted by, for example, selection of pulp fibers, a pretreatment, or defibration.

The degree of crystallinity is a value measured by an X-ray diffraction method conforming to JIS-K0131 (1996) "General rules for X-ray diffraction analysis". Note that the fine cellulose fibers have an amorphous portion and a crystalline portion, and the degree of crystallinity means the ratio of the crystalline portion in the entire fine cellulose fibers.

The light transmittance of the fine cellulose fibers (solution having a solid content of 0.2%) is preferably 40.0% or more, more preferably 60.0% or more, and particularly preferably 70.0%. When the light transmittance is less than 40.0%, transparency may be insufficient. The light transmittance of the fine cellulose fibers can be adjusted by, for example, selection of pulp fibers, a pretreatment, or defibration.

The light transmittance is a value obtained by measuring the transparency (transmittance of light of 350 to 880 nm) of a 0.2% (w/v) fine cellulose fiber dispersion using a spectrophotometer U-2910 (Hitachi, Ltd.).

When the concentration of the fine cellulose fibers is 1% by mass (w/w), the B-type viscosity of the dispersion is preferably 10 to 300,000 cps, more preferably 1,000 to 200,000 cps, and particularly preferably 10,000 to 100,000 cps.

The B-type viscosity is a value measured for an aqueous dispersion of fine cellulose fibers having a solid concentration of 1% conforming to JIS-Z8803 (2011) "Method for measuring viscosity of liquid". The B-type viscosity is a resistance torque when a slurry is stirred, and a higher B-type viscosity means that more energy is required for stirring.

(Method for Manufacturing Fine Cellulose Fibers)

In the manufacturing method of the present embodiment, an alkali metal ion-containing substance and an additive (A) containing at least one of a phosphorous acid and a metal phosphite is added to cellulose fibers, preferably sodium hydrogen phosphite are added thereto. The resulting mixture is heated to introduce a phosphite containing a cation of an inorganic substance into the cellulose fibers. More preferably, an additive (B) containing at least one of urea and a urea derivative is further added. The resulting mixture is heated to introduce a phosphite containing a cation of an inorganic substance and a carbamate into the cellulose fibers. The cellulose fibers into which a phosphite containing a cation of an inorganic substance or the like is introduced are washed and defibrated into fine cellulose fibers.

(Cellulose Fibers)

Examples of the cellulose fibers include plant-derived fibers (plant fibers), animal-derived fibers, and microorganism-derived fibers. These fibers can be used singly or in combination of two or more types thereof as necessary. However, as the cellulose fibers, plant fibers are preferably used, and pulp fibers which are a kind of plant fibers are more preferably used. When pulp fibers are used as the cellulose fibers, the physical properties of the fine cellulose fibers are easily adjusted.

Examples of the plant fibers include a wood pulp made from hardwood or softwood, a non-wood pulp made from straw or bagasse, and a de-inked pulp (DIP) made from recovered used paper or waste paper. These fibers can be used singly or in combination of two or more types thereof.

Examples of the wood pulp include a chemical pulp such as a hardwood kraft pulp (LKP) or a softwood kraft pulp (NKP), a mechanical pulp (TMP), and a de-inked pulp (DIP). These pulps can be used singly or in combination of two or more types thereof.

The hardwood kraft pulp (LKP) may be a hardwood bleached kraft pulp, a hardwood unbleached kraft pulp, or a hardwood semibleached kraft pulp. The softwood kraft pulp (NKP) may be a softwood bleached kraft pulp, a softwood unbleached kraft pulp, or a softwood semibleached kraft pulp. The de-inked pulp (DIP) may be a magazine de-inked pulp (MDIP), a newspaper de-inked pulp (NDIP), a corrugated de-inked pulp (WP), or another de-inked pulp.

Note that cellulose fibers as natural fibers (cellulose fibers before defibration) generally have a fiber width of about 20 to 30 μm. A cellulose fiber having such a fiber width becomes a fine cellulose fiber having a fiber width of 1 μm or less by defibration or the like.

(Alkali Metal Ion-Containing Substance)

Examples of the alkali metal ion-containing substance include a hydroxide, a metal sulfate, a metal nitrate, a metal chloride, a metal phosphate, a metal phosphite, and a metal carbonate. However, a metal phosphite also serving as the additive (A) is preferably used, and a sodium hydrogen phosphite is more preferably used. Note that as described above, the addition of the alkali metal ion-containing substance can be performed not only in the step of introducing a phosphite but also in a step such as the defibration step, the concentration step, or the aggregation step, or between these steps (before the step of introducing a phosphite, after the step of introducing a phosphite, before the defibration step, after the defibration step, before the concentration step, or the like).

(Additive (A))

The additive (A) contains at least one of a phosphorous acid and a metal phosphite. Examples of the additive (A) include a phosphorous acid compound such as phosphorous acid, sodium hydrogen phosphite, ammonium hydrogen phosphite, potassium hydrogen phosphite, sodium dihydrogen phosphite, sodium phosphite, lithium phosphite, potassium phosphite, magnesium phosphite, calcium phosphite, triethyl phosphite, triphenyl phosphite, or pyrophosphorous acid. These phosphorous acids and metal phosphites can be used singly or in combination of two or more types thereof. However, sodium hydrogen phosphite also serving as an alkali metal ion-containing substance is preferably used.

When the additive (A) is added, the cellulose fibers may be in a dry state, a wet state, or a slurry state. The additive (A) may be in a powdery state or an aqueous solution state. However, it is preferable to add the additive (A) in an aqueous solution state to the cellulose fibers in a dry state due to high uniformity of a reaction.

The addition amount of the additive (A) is preferably 1 to 10,000 g, more preferably 100 to 5,000 g, and particularly preferably 300 to 1,500 g with respect to 1 kg of cellulose fibers. When the addition amount is less than 1 g, the effect of addition of the additive (A) is not necessarily obtained. Meanwhile, even when the addition amount exceeds 10,000 g, the effect of addition of the additive (A) may reach a plateau.

(Additive (B))

The additive (B) contains at least one of urea and a urea derivative. Examples of the additive (B) include urea, thiourea, biuret, phenylurea, benzylurea, dimethylurea, diethylurea, and tetramethylurea. The urea and urea derivatives can be used singly or in combination of two or more types thereof. However, urea is preferably used.

When being heated, the additive (B) is decomposed into isocyanic acid and ammonia as indicated in the following reaction formula (1). Isocyanic acid is very reactive, and reacts with a hydroxyl group of cellulose to form a carbamate as indicated in the following reaction formula (2).

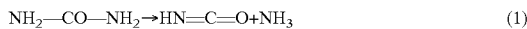  (1)

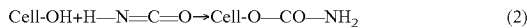  (2)

The addition amount of the additive (B) is preferably 0.01 to 100 mol, more preferably 0.2 to 20 mol, and particularly preferably 0.5 to 10 mol with respect to 1 mol of the additive (A). When the addition amount is less than 0.01 mol, a carbamate is not necessarily introduced into the cellulose fibers sufficiently. Meanwhile, even when the addition amount exceeds 100 mol, the effect of addition of urea may reach a plateau.

(Heating)

When the cellulose fibers including the additive are heated, heating temperature is preferably 100 to 210° C., more preferably 100 to 200° C., and particularly preferably 100 to 180° C. When the heating temperature is 100° C. or higher, a phosphite can be introduced. However, when the heating temperature exceeds 210° C., deterioration of cellulose proceeds rapidly, which may cause coloring and a decrease in viscosity.

When the cellulose fibers including the additive are heated, the pH is preferably 3 to 12, more preferably 4 to 11, and particularly preferably 6 to 9. A lower pH makes it easier to introduce a phosphite and a carbamate. However, when the pH is less than 3, deterioration of cellulose may proceed rapidly.

The heating of the cellulose fibers including the additive is preferably performed until the cellulose fibers are dried. Specifically, drying is performed until the moisture content of the cellulose fibers becomes preferably 10% or less, more preferably 0.1% or less, and particularly preferably 0.001% or less. Of course, the cellulose fibers may be in a completely dry state without moisture.

Heating time of the cellulose fibers including the additive is, for example, 1 to 1,440 minutes, preferably 10 to 180 minutes, and more preferably 30 to 120 minutes. When the heating time is too long, the introduction of a phosphite or a carbamate may proceed excessively. When the heating time is too long, the cellulose fibers may turn yellow.

Examples of an apparatus for heating the cellulose fibers including the additive include a hot air dryer, a paper machine, and a dry pulp machine.

(Pretreatment)

Prior to introduction of a phosphite containing a cation of an inorganic substance or the like into the cellulose fibers, and/or after introduction of a phosphite containing a cation of an inorganic substance or the like into the cellulose fibers, a pretreatment such as beating can be performed on the cellulose fibers as necessary. By performing a pretreatment on the pulp fibers prior to defibration of the cellulose fibers, the number of times of defibration can be significantly reduced, and energy required for the defibration can be reduced.

The pretreatment of the cellulose fibers can be performed by a physical method or a chemical method, preferably by a physical method and a chemical method. The pretreatment by a physical method and the pretreatment by a chemical method can be performed simultaneously or separately.

As the pretreatment by the physical method, beating is preferably adopted. When the cellulose fibers are beaten, the cellulose fibers are trimmed. Therefore, entanglement between the cellulose fibers is prevented (prevention of aggregation). Beating is performed preferably until freeness of the cellulose fibers becomes 700 ml or less, more preferably until the freeness of the cellulose fibers becomes 500 ml or less, and particularly preferably until the freeness of the cellulose fibers becomes 300 ml or less from this viewpoint. The freeness of the cellulose fibers is a value measured conforming to JIS P8121-2 (2012). Beating can be performed using, for example, a refiner or a beater.

Examples of the pretreatment by a chemical method include hydrolysis of a polysaccharide by an acid (acid treatment), hydrolysis of a polysaccharide by an enzyme (enzyme treatment), swelling of a polysaccharide by an alkali (alkali treatment), oxidation of a polysaccharide by an oxidizing agent (oxidation treatment), and reduction of a polysaccharide by a reducing agent (reduction treatment). However, as the pretreatment by a chemical method, the enzyme treatment is preferably performed, and one or more treatments selected from the acid treatment, the alkali treatment, and the oxidation treatment are more preferably performed in addition thereto. Hereinafter, the enzyme treatment and the alkali treatment will be described in order.

As an enzyme used for the enzyme treatment, at least one of a cellulase-based enzyme and a hemicellulase-based enzyme is preferably used, and both of these enzymes are more preferably used together. Use of these enzymes makes defibration of the cellulose fibers easier. Note that the cellulase-based enzyme causes decomposition of cellulose in the presence of water. The hemicellulase-based enzyme causes decomposition of hemicellulose in the presence of water.

Examples of the cellulase-based enzyme include enzymes that produce *Trichoderma* (filamentous fungus), *Acremonium* (filamentous fungus), *Aspergillus* (filamentous fungus), *Phanerochaete* (basidiomycete), *Trametes* (basidiomycete), *Humicola* (filamentous fungus), *Bacillus* (bacterium), *Schizophyllum* (basidiomycete), *Streptomyces* (bacterium), and *Pseudomonas* (bacterium). These cellulase-based enzymes can be purchased as reagents or commercially available products. Examples of the commercially available products include Cellulosin T2 (manufactured by HBI Inc.), Meicelase (manufactured by Meiji Seika Co., Ltd.), Novozyme 188 (manufactured by Novozyme), Multifect CX10L (manufactured by Genencor Corp.), and cellulase-based enzyme GC220 (manufactured by Genencor Corp.).

In addition, as the cellulase-based enzyme, either endoglucanase (EG) or cellobiohydrolase (CBH) can also be used. EG and CBH may be used singly or as a mixture thereof. In addition, EG and CBH may be mixed with a hemicellulase-based enzyme to be used.

Examples of the hemicellulase-based enzyme include xylanase as an enzyme that decomposes xylan, mannase as an enzyme that decomposes mannan, and arabanase as an enzyme that decomposes araban. Pectinase as an enzyme that decomposes pectin can also be used.

Hemicellulose is a polysaccharide excluding a pectin, which is between cellulose microfibrils in a plant cell wall. Hemicellulose is diverse and differs depending on the kind of wood and a cell wall layer. Glucomannan is the main component on a secondary wall of softwood, and 4-O-methylglucuronoxylan is a main component on a secondary wall of hardwood. Therefore, when fine cellulose fibers are obtained from a softwood bleached kraft pulp (NBKP), mannase is preferably used. When fine cellulose fibers are obtained from a hardwood bleached kraft pulp (LBKP), xylanase is preferably used.

The addition amount of an enzyme to the cellulose fibers depends on, for example, the kind of the enzyme, the kind of wood as a raw material (softwood or hardwood), or the kind of mechanical pulp. However, the addition amount of an enzyme to the cellulose fibers is preferably 0.1 to 3% by mass, more preferably 0.3 to 2.5% by mass, and particularly preferably 0.5 to 2% by mass. When the addition amount of an enzyme is less than 0.1% by mass, the effect of addition of the enzyme is not necessarily obtained sufficiently. Meanwhile, when the addition amount of an enzyme exceeds 3% by mass, cellulose is saccharified, and the yield of the fine cellulose fibers may be reduced. In addition, an effect corresponding to the increase in the addition amount cannot be improved disadvantageously.

When a cellulase-based enzyme is used as the enzyme, the pH during the enzyme treatment is preferably within a weakly acidic region (pH=3.0 to 6.9) from a viewpoint of reactivity of an enzyme reaction. Meanwhile, when a hemicellulase-based enzyme is used as the enzyme, the pH during the enzyme treatment is preferably within a weakly alkaline region (pH=7.1 to 10.0).

Temperature during the enzyme treatment is preferably 30 to 70° C., more preferably 35 to 65° C., and particularly preferably 40 to 60° C., regardless of whether a cellulase-based enzyme or a hemicellulase-based enzyme is used as the enzyme. When the temperature during the enzyme treatment is 30° C. or higher, enzyme activity is hardly reduced, and prolongation of treatment time can be prevented. Meanwhile, when the temperature during the enzyme treatment is 70° C. or lower, deactivation of the enzyme can be prevented.

The time of the enzyme treatment depends on, for example, the kind of enzyme, the temperature of the enzyme treatment, or the pH during the enzyme treatment. However, in general, the time of the enzyme treatment is 0.5 to 24 hours.

After the enzyme treatment, the enzyme is preferably deactivated. Examples of a method for deactivating the enzyme include a method for adding an aqueous alkaline solution (preferably having a pH of 10 or more, more preferably a pH of 11 or more) and a method for adding hot water at 80 to 100° C.

Next, a method of the above-described alkali treatment will be described.

Examples of the method of the alkali treatment include a method for immersing cellulose fibers into which a phosphite or the like is introduced in an alkaline solution.

An alkali compound contained in the alkaline solution may be an inorganic alkali compound or an organic alkali compound. Examples of the inorganic alkali compound include a hydroxide of an alkali metal or an alkaline earth metal, a carbonate of an alkali metal or an alkaline earth metal, and a phosphate of an alkali metal or an alkaline earth metal. Examples of the hydroxide of an alkali metal include lithium hydroxide, sodium hydroxide, and potassium hydroxide. Examples of the hydroxide of an alkaline earth metal include calcium hydroxide. Examples of the carbonate of an alkali metal include lithium carbonate, lithium hydrogen carbonate, potassium carbonate, potassium hydrogen carbonate, sodium carbonate, and sodium hydrogen carbonate. Examples of the carbonate of an alkaline earth metal include calcium carbonate. Examples of the phosphate of an alkali metal include lithium phosphate, potassium phosphate, trisodium phosphate, and disodium hydrogen phosphate. Examples of the phosphate of an alkaline earth metal include calcium phosphate and calcium hydrogen phosphate.

Examples of the organic alkali compound include ammonia, an aliphatic amine, an aromatic amine, an aliphatic ammonium, an aromatic ammonium, a heterocyclic compound and a hydroxide thereof, a carbonate, and a phosphate. Specific examples of the organic alkali compound include ammonia, hydrazine, methylamine, ethylamine, diethylamine, triethylamine, propylamine, dipropylamine, butylamine, diaminoethane, diaminopropane, diaminobutane, diaminopentane, diaminohexane, cyclohexylamine, aniline, tetramethylammonium hydroxide, tetraethylammonium hydroxide, tetrapropylammonium hydroxide, tetrabutylammonium hydroxide, benzyltrimethylammonium hydroxide, pyridine, N,N-dimethyl-4-aminopyridine, ammonium carbonate, ammonium hydrogen carbonate, and diammonium hydrogen phosphate.

A solvent of the alkaline solution may be either water or an organic solvent, but is preferably a polar solvent (a polar organic solvent such as water or an alcohol), and more preferably an aqueous solvent containing at least water.

The pH of the alkaline solution at 25° C. is preferably 9 or more, more preferably 10 or more, and particularly preferably 11 to 14. When the pH is 9 or more, the yield of the fine cellulose fibers is high. However, when the pH exceeds 14, handleability of the alkaline solution decreases.

(Washing)

The cellulose fibers into which a phosphite or the like is introduced are preferably washed prior to defibration. By washing the cellulose fibers, by-products and unreacted substances can be washed away. If the washing is performed prior to the alkali treatment in the pretreatment, the amount of the alkaline solution used in the alkali treatment can be reduced.

The cellulose fibers can be washed using, for example, water or an organic solvent.

(Defibration)

The cellulose fibers into which a phosphite or the like is introduced are washed and then defibrated (made finer). By this defibration, the pulp fibers are microfibrillated and become fine cellulose fibers.

Before the cellulose fibers are defibrated, the cellulose fibers are preferably formed into a slurry state. The solid concentration of this slurry is preferably 0.1 to 20% by mass, more preferably 0.5 to 10% by mass, and particularly preferably 1.0 to 5.0% by mass. When the solid concentration is within the above range, the fibers can be efficiently defibrated.

The cellulose fibers can be defibrated, for example, by using one or more means selected from a homogenizer such as a high-pressure homogenizer or a high-pressure homogenizing apparatus, a high-speed rotary homogenizer, a stone mill type friction machine such as a grinder or a grinding machine, a refiner such as a conical refiner or a disc refiner, a uniaxial kneader, a multiaxial kneader, and various bacteria. However, the cellulose fibers are preferably defibrated using an apparatus/method for making the cellulose fibers finer by a water flow, particularly by a high-pressure water flow. According to this apparatus/method, dimensional uniformity and dispersion uniformity of the obtained fine cellulose fibers are extremely high. In contrast, for example, when a grinder that performs grinding between rotating grindstones is used, it is difficult to make the cellulose fibers finer uniformly, and a fiber mass that cannot be defibrated may partly remain in some cases.

Examples of a grinder used for defibrating the cellulose fibers include Masscolloider manufactured by Masuko Sangyo Co., Ltd. Examples of an apparatus for making the cellulose fibers finer by a high-pressure water flow include Starburst (registered trademark) manufactured by Sugino Machine Co., Ltd. and Nanovater (registered trademark) manufactured by Yoshida Machine Industry Co., Ltd. Examples of a high-speed rotary homogenizer used for defibrating the cellulose fibers include CLEARMIX-11S manufactured by M Technique Co., Ltd.

Note that the present inventors have found that cellulose fibers obtained by defibration by a method for making the cellulose fibers finer by a high-pressure water flow have a more uniform fiber width than cellulose fibers obtained by a method for performing grinding between rotating grindstones by observation of the obtained fibers with a microscope.

Defibration by a high-pressure water flow is suitably performed by pressurizing a dispersion of the cellulose fibers with a pressure intensifier, for example, to 30 MPa or more, preferably 100 MPa or more, more preferably 150 MPa or more, particularly preferably 220 MPa or more (high pressure condition), ejecting the dispersion from a nozzle having a pore diameter of 50 μm or more to reduce the pressure such that a pressure difference is, for example, 30 MPa or more, preferably 80 MPa or more, and more preferably 90 MPa or more (pressure reduction condition). Pulp fibers are defibrated by a cleavage phenomenon caused by this pressure difference. When a pressure under the high pressure condition is low, or when a pressure difference from the high pressure condition to the pressure reduction condition is small, defibration efficiency decreases, and it is necessary to repeatedly perform defibration (eject the cellulose fibers from the nozzle) in order to obtain a desired fiber width.

As an apparatus for defibration by a high-pressure water flow, a high-pressure homogenizer is preferably used. The high-pressure homogenizer refers to a homogenizer capable of ejecting a slurry of cellulose fibers at a pressure of, for example, 10 MPa or more, preferably 100 MPa or more. When the cellulose fibers are treated with a high-pressure homogenizer, collisions between the cellulose fibers, a pressure difference, microcavitation and the like occur, and defibration of the cellulose fibers occurs effectively. Therefore, the number of times of defibration can be reduced, and manufacturing efficiency of the fine cellulose fibers can be increased.

As the high-pressure homogenizer, a high-pressure homogenizer that causes counter collision of a slurry of the cellulose fibers on a straight line is preferably used. Specific examples of the high-pressure homogenizer include a counter collision type high-pressure homogenizer (MICROFLUIDIZER (registered trademark), wet jet mill). In this apparatus, two upstream flow paths are formed such that the pressurized slurry of the cellulose fibers causes counter collision at a junction. The slurry of the cellulose fibers causes collision at the junction, and the slurry of the cellulose fibers that has caused collision flows out of a downstream flow path. The downstream flow path is formed perpendicular to the upstream flow paths, and the upstream flow paths and the downstream flow path form a T-shaped flow path. By using such a counter collision type high-pressure homogenizer, energy imparted from the high-pressure homogenizer is converted into collision energy to the maximum. Therefore, the cellulose fibers can be more efficiently defibrated.

The cellulose fibers are preferably defibrated such that the average fiber width, average fiber length, degree of water retention, degree of crystallinity, peak value of a pseudo particle size distribution, and pulp viscosity of the obtained fine cellulose fibers are the above-described desired values or evaluated as described above.

(Concentration)

The dispersion containing the fine cellulose fibers into which a phosphite containing a cation of an inorganic substance is introduced is concentrated to be formed into a fine cellulose fiber-containing substance. In the present embodiment, an alkali metal ion-containing substance is added in order to obtain the fine cellulose fibers, and the obtained fine cellulose fiber-containing substance contains a cation of an inorganic substance. Therefore, this concentration is extremely easy.

The concentration of the fine cellulose fibers is preferably performed such that the moisture content is less than 90% by mass, and particularly preferably performed such that the moisture content is less than 80% by mass. When concentration is performed such that the moisture content exceeds 90% by mass, the concentration may be insufficient for solving the problem of transportation energy.

As a concentration method (dehydration method, drying method, or the like), for example, one or a combination of two or more selected from rotary kiln drying, disk drying, air flow drying, medium fluid drying, spray drying, drum drying, screw conveyor drying, paddle drying, uniaxial kneading drying, multiaxial kneading drying, vacuum drying, and stirring drying can be adopted. However, drum drying is preferably adopted.

(Aggregation)

The step of obtaining a fine cellulose fiber-containing substance from a dispersion containing fine cellulose fibers into which a phosphite containing a cation of an inorganic substance is introduced may include a step of aggregating the fine cellulose fibers. As an aggregating agent that performs this aggregation (aggregates the fine cellulose fibers), for example, one or a combination of two or more selected from an alcohol, a metal salt, an acid, a cationic surfactant, and a cationic polymer aggregating agent can be used.

Examples of the alcohol as the aggregating agent include a lower alcohol, a polyhydric alcohol, and an aliphatic alcohol. Specifically, for example, one or a combination of two or more selected from methanol, ethanol, isopropanol, butanol, ethylene glycol, glycerin, octanol, dodecanol, tetradecanol, cetanol, octadecyl alcohol, and oleyl alcohol can be used.

The addition amount of the alcohol as the aggregating agent is preferably 1 to 100,000 g, and more preferably 10 to 10,000 g with respect to 1 kg of the fine cellulose fibers.

As the metal salt as the aggregating agent, for example, one or a combination of two or more selected from aluminum sulfate, magnesium sulfate, calcium sulfate, sodium sulfate, polyferric sulfate, sodium chloride, aluminum chloride, magnesium chloride, calcium chloride, polyaluminum chloride, lithium phosphate, sodium phosphate, potassium phosphate, sodium phosphite, lithium phosphite, and potassium phosphite can be used.

The addition amount of the metal salt as the aggregating agent is preferably 1 to 100,000 g, and more preferably 10 to 10,000 g with respect to 1 kg of fine cellulose fibers.

The acid as the aggregating agent may be either an inorganic acid or an organic acid. As the inorganic acid, for example, one or a combination of two or more selected from hydrochloric acid, nitric acid, sulfuric acid, phosphoric acid, and phosphorous acid can be used. As the organic acid, for example, one or a combination of two or more selected from glycolic acid, lactic acid, tartronic acid, glyceric acid, hydroxybutyric acid, malic acid, tartaric acid, citric acid, isocitric acid, mevalonic acid, pantoic acid, ricinoleic acid, stearic acid, maleic acid, formic acid, and acetic acid can be used.

When an acid is added to the fine cellulose fibers, the pH is preferably 4.0 or less. However, when the pH is 1.0 or less, there is a concern that the physical properties of the fine cellulose fibers may decrease due to hydrolysis.

As the cationic surfactant as the aggregating agent, for example, one or a combination of two or more selected from a quaternary ammonium salt (stearyltrimethylammonium chloride, behenyltrimethylammonium chloride, distearyldimethylammonium chloride, ethylsulfatelanolinfatty acid aminopropylethyldimethylammonium, or the like), and an amine salt (diethylaminoethylamide stearate lactate, dilaurylamine hydrochloride, oleylamine lactate, or the like) can be used.

The addition amount of the cationic surfactant is preferably 1 to 100,000 g, and more preferably 10 to 10,000 g with respect to 1 kg of the fine cellulose fibers.

As the cationic polymer aggregating agent as the aggregating agent, for example, one or a combination of two or more selected from a homopolymer of a cationic monomer, a copolymer of a cationic monomer and a nonionic monomer, a condensation-based polyamine, a polyvinylamine, a polyvinylamidine, a poly (meth)allylamine, a dicyandiamide/formalin condensate, polyethylene imine, polyvinyl imidazoline, polyvinyl pyridine, a diallylamine salt/sulfur dioxide copolymer, a polydimethyldiallylammonium salt/sulfur dioxide copolymer, a polydimethyldiallylammonium salt, a polydimethyldiallylammonium salt/polyacrylamide copolymer, and an allylamine salt polymer can be used.

The addition amount of the cationic polymer aggregating agent is preferably 1 to 100,000 g, and more preferably 10 to 10,000 g with respect to 1 kg of the fine cellulose fibers.

(Redispersing Agent)

The fine cellulose fiber-containing substance may contain a redispersing agent that enhances redispersion in water. When the fine cellulose fiber-containing substance contains a redispersing agent, it is considered that hydrogen bonding between the fine cellulose fibers is weakened, and dispersion between the fine cellulose fibers is accelerated by an electrostatic repulsion or an osmotic effect in water.

It is desirable that the redispersing agent is a hydroxy acid, a hydroxy acid salt, glycerin, or a glycerin derivative.

(Redispersing Method)

When the fine cellulose fiber-containing substance is redispersed in water, for example, one or a combination of two or more selected from a magnetic stirrer, an agitator, a propeller mixer, a homomixer, a homogenizer, a pipeline mixer, a turbine mixer, and a paddle mixer can be used.

(Fine Cellulose Fiber Dispersion)

The fine cellulose fiber-containing substance can be formed into a fine cellulose fiber dispersion simply by being mixed with water.

EXAMPLES

Next, Examples of the present invention will be described.

A test was performed to confirm redispersibility of the fine cellulose fiber-containing substance according to the present embodiment. The fine cellulose fiber-containing substance was redispersed in water so as to have a concentration of 1.0% by mass. Details are as follows.

Test Example 1

13 g of sodium hydrogen phosphite pentahydrate, 10.8 g of urea, and 76.2 g of water were mixed to manufacture reagent A. 100 g of the manufactured reagent A and 10 g of a dry raw material pulp (NBKP: moisture: 98.0% by mass) were mixed and dried at 105° C. The dry pulp was caused to react at 130° C. for two hours. Washing with water and filtration were repeated twice to obtain cellulose fibers (phosphorous acid-modified pulp) into which a phosphite containing a cation of an inorganic substance was introduced. The obtained phosphorous acid-modified pulp was diluted with distilled water so as to have a solid content of 10% by mass to obtain a phosphorous acid-modified pulp slurry (dispersion). The phosphorous acid-modified pulp slurry was pre-beaten at 9200 rpm using a PFI mill. The pre-beaten phosphorous acid-modified pulp slurry was adjusted so as to have a solid concentration of 1%, and defibrated twice using a high-pressure homogenizer to obtain an aqueous dispersion of fine cellulose fibers having a concentration of 1.0% by mass. This aqueous dispersion of fine cellulose fibers having a concentration of 1.0% by mass was dried at 105° C. for six hours to obtain a film-like fine cellulose fiber-containing substance (dry product). The fine cellulose fiber-containing substance had a moisture content of 9.8% by mass.

To the fine cellulose fiber-containing substance obtained as described above, water was added such that the solid concentration was 1.0% by mass. The resulting mixture was stirred at 800 rpm for 60 minutes using a magnetic stirrer to obtain a redispersion of the fine cellulose fiber-containing substance. The obtained redispersion was allowed to stand for 10 minutes, and then the concentration of the supernatant was measured. Table 1 indicates the concentration of the supernatant (%), the amount of sodium (mmol), and the degree of substitution (DS).

Test Examples 2 to 5

Test Example 2 was performed in a similar manner to Test Example 1 except that 0.22 g of sodium hydroxide was added to the pre-beaten but not defibrated phosphorous acid-modified pulp slurry before being formed into the fine cellulose fiber-containing substance (dry product).

Test Example 3 was performed in a similar manner to Test Example 1 except that the dry pulp was caused to react at 140° C. for two hours.

Test Example 4 was performed in a similar manner to Test Example 1 except that the dry pulp was caused to react at 170° C. for two hours.

Test Example 5 was performed in a similar manner to Test Example 1 except that the dry pulp was caused to react at 180° C. for two hours.

Note that in Test Examples 3 to 5, the amount of sodium was changed by changing the reaction temperature of the dry pulp as described above.

TABLE 1

|  | Concentration of supernatant % | Amount of sodium mmol/g | Degree of substitution (DS) |
|---|---|---|---|
| Test Example 1 | 0.4 | 0.14 | 0.14 |
| Test Example 2 | 0.6 | 0.69 | 0.14 |
| Test Example 3 | 0.7 | 0.85 | 0.16 |
| Test Example 4 | 0.9 | 1.15 | 0.25 |
| Test Example 5 | 1.0 | 2.36 | 0.28 |

(Discussion)

From the test results, it has been found that the redispersibility increases as the amount of sodium increases. Note that the degrees of substitution (DS) of a phosphite group in Test Examples 1 and 2 were the same value of 0.14.

INDUSTRIAL APPLICABILITY

The present invention can be used as a fine cellulose fiber-containing substance, a method for manufacturing the same, and a method for manufacturing a fine cellulose fiber dispersion.

The invention claimed is:

1. A fine cellulose fiber-containing substance comprising fine cellulose fibers into which a phosphite containing a cation of an inorganic substance is introduced,
    wherein a ratio of the cation of the inorganic substance with respect to 1 g of the fine cellulose fibers is 0.14 mmol or more.

2. The fine cellulose fiber-containing substance according to claim 1,
    wherein the fine cellulose fibers each have a fiber width of 1 to 1000 nm, and
    functional groups represented by the following structural formula (1) are substituted for a part of hydroxy groups of the cellulose fibers to introduce a phosphite containing the cation of the inorganic substance:

[Chemical formula 1]

Structural formula (1)

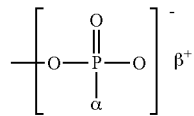

wherein α represents any one of nothing, R, and NHR, R represents any one of a hydrogen atom, a saturated-linear hydrocarbon group, a saturated-branched hydrocarbon group, a saturated-cyclic hydrocarbon group, an unsaturated-linear hydrocarbon group, an unsaturated-branched hydrocarbon group, an aromatic group, and a derived group thereof, and β represents a cation of an inorganic substance.

3. The fine cellulose fiber-containing substance according to claim 2, wherein the cation of the inorganic substance is an alkali metal ion or an alkaline earth metal ion.

4. The fine cellulose fiber-containing substance according to claim 2, having a moisture content of less than 90% by mass.

5. The fine cellulose fiber-containing substance according to claim 1, wherein the cation of the inorganic substance is an alkali metal ion or an alkaline earth metal ion.

6. The fine cellulose fiber-containing substance according to claim 5, having a moisture content of less than 90% by mass.

7. The fine cellulose fiber-containing substance according to claim 1, having a moisture content of less than 90% by mass.

* * * * *

UNITED STATES PATENT AND TRADEMARK OFFICE
CERTIFICATE OF CORRECTION

PATENT NO. : 11,220,787 B2  
APPLICATION NO. : 16/632799  
DATED : January 11, 2022  
INVENTOR(S) : Ikko Matsusue Page 1 of 1

It is certified that error appears in the above-identified patent and that said Letters Patent is hereby corrected as shown below:

In the Claims

Column 16, Line 36 of Claim 2:  
"wherein a represents..."  
Should instead read:  
--wherein α represents...--

Column 16, Line 42 of Claim 2:  
"...f3 represents..."  
Should instead read:  
--...β represents...--

Signed and Sealed this  
Fifth Day of April, 2022

Drew Hirshfeld  
*Performing the Functions and Duties of the*  
*Under Secretary of Commerce for Intellectual Property and*  
*Director of the United States Patent and Trademark Office*